United States Patent [19]
Morrison

[11] Patent Number: 5,584,818
[45] Date of Patent: Dec. 17, 1996

[54] SAFETY HYPODERMIC NEEDLE AND SHIELDING CAP ASSEMBLY

[76] Inventor: David Morrison, 1711 Highway 17, South, OSV #641, 1719 E. Lake Dr., Surfside Beach, S.C. 29575

[21] Appl. No.: 533,332

[22] Filed: Sep. 25, 1995

Related U.S. Application Data

[63] Continuation-in-part of Ser. No. 293,730, Aug. 22, 1994, abandoned.

[51] Int. Cl.⁶ ..................................................... A61M 5/32
[52] U.S. Cl. ........................ 604/197; 604/192; 604/198; 604/110
[58] Field of Search ................................... 604/192–198, 604/110, 263; 128/919

[56] References Cited

U.S. PATENT DOCUMENTS

| | | | |
|---|---|---|---|
| 4,850,977 | 7/1989 | Bayless | 604/198 |
| 4,955,866 | 9/1990 | Corey | 604/192 |
| 5,334,149 | 8/1994 | Nortman et al. | 604/110 |
| 5,348,544 | 9/1994 | Sweeney et al. | 604/192 |
| 5,395,347 | 3/1995 | Blecher et al. | 604/198 |
| 5,423,766 | 6/1995 | Di Cesare | 604/192 |

*Primary Examiner*—Randall L. Green
*Assistant Examiner*—V. Alexander
*Attorney, Agent, or Firm*—Hinkle & Associates, P.C.

[57] ABSTRACT

A safety hypodermic needle and shielding device has a spring-loaded safety shield (1) with a one-way locking device (18, 21) which prevents return travel of the safety shield in a direction towards a syringe (3). This prevents exposure of a needle point (15) that has been used. A preferred one-way locking device is a pivot plate (18) positioned in the shielding device with the syringe-needle cannula shaft (2) extended through a locking orifice (20) in the pivot plate. For low-angle use of the syringe, a spring for spring-loading the shielding device is at least one leaf spring (17 or 17a) having expansion in a plane parallel to the syringe-needle shaft. A cannula sheath (14) has a cannula skirt (13) that is positioned in locking relationship to a quick-release latch (6, 24, 30) as a safety lock prior to use. A shield on another embodiment uses a concave flat, elongated spring (17a) to act as a resistant column to prevent the safety shield from being pushed to expose the needle point once the syringe has been used.

4 Claims, 4 Drawing Sheets

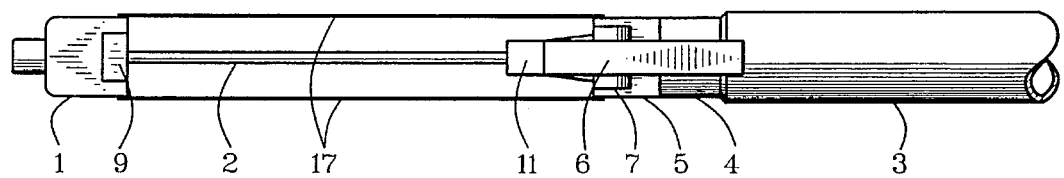
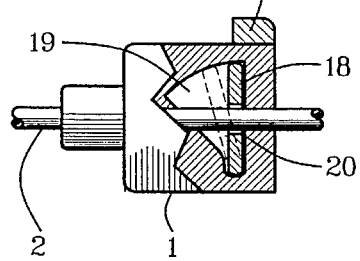
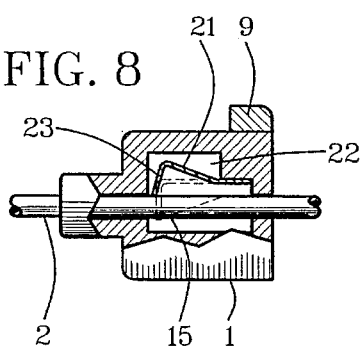
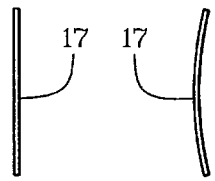
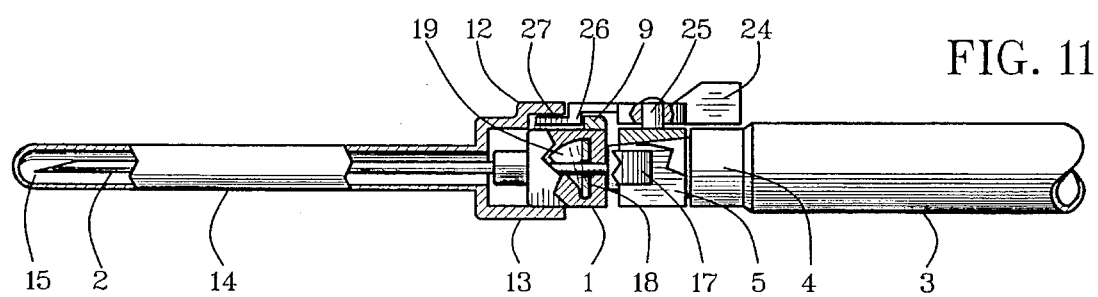
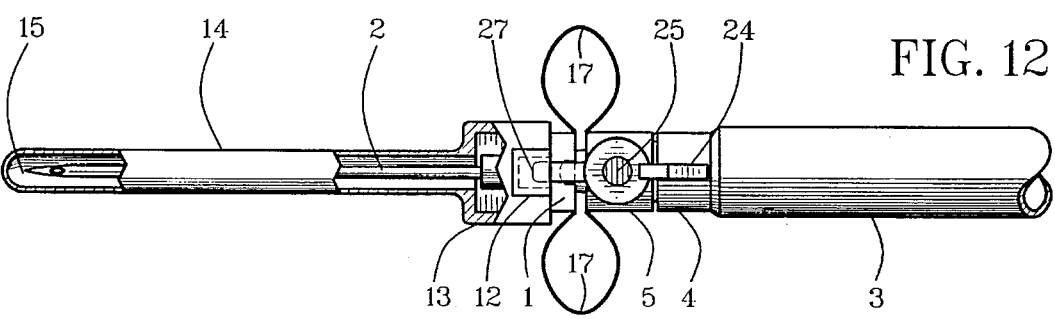
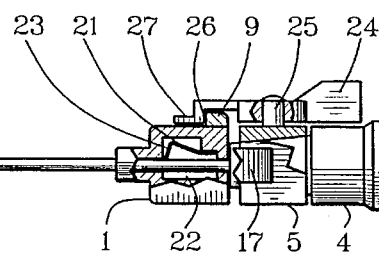

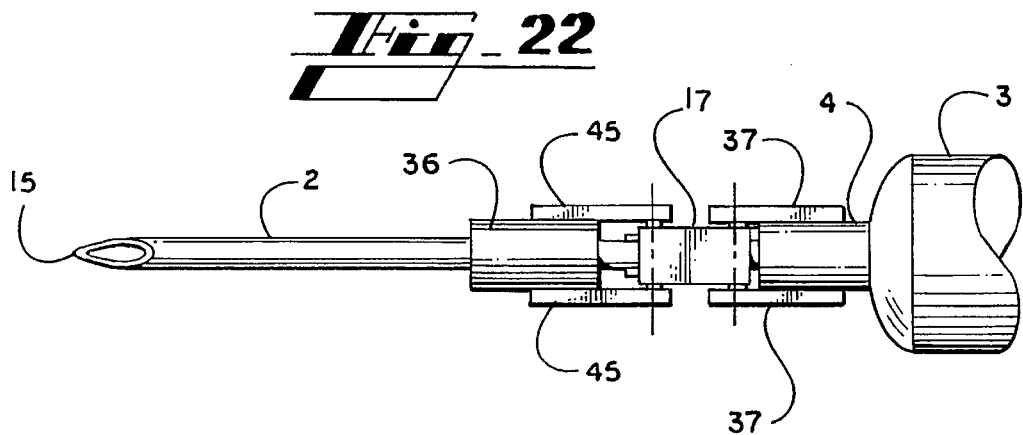
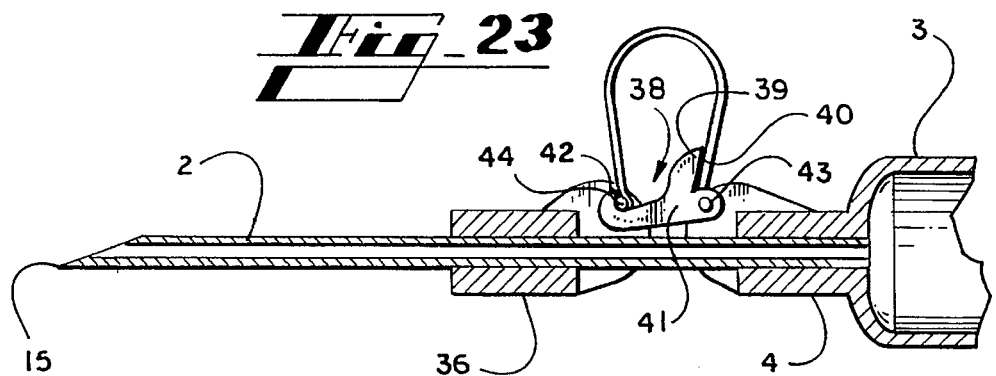
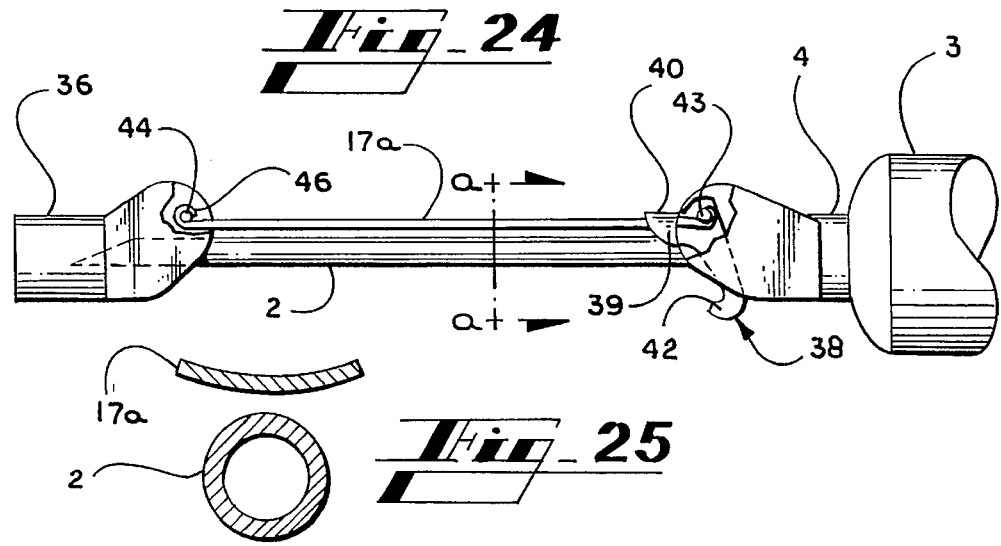

5,584,818

SAFETY HYPODERMIC NEEDLE AND SHIELDING CAP ASSEMBLY

This application is a continuation-in-part of application Ser. No. 08/293,730, filed Aug. 22, 1994, now abandoned.

BACKGROUND OF THE INVENTION

I. Field of the Invention

The present invention relates generally to the field of hypodermic syringes and in particular to a spring-loaded safety shield which attaches to a conventional hypodermic needle in a manner that a syringe and the safety shield to which the hypodermic needle is attached can be used conveniently and the safety shield can be released easily with one hand after use to allow the spring-loaded safety shield to travel towards a point end and to lock onto the syringe needle if and wherever stopped along the needle and then, after reaching the point end, to lock onto it in order to prevent needle-stick contact with the point end and to prevent reuse of the syringe needle, or possibly make it difficult to reuse the needle.

II. Description of the Prior Art

The onslaught of the AIDS epidemic has caused a growing concern for what has come to be known as "needle-stick" injury with life-threatening consequences to health-care workers. It has caused concern also for safety of individuals who may be contacted by and who may use hypodermic needles that have been used previously. The concern is so great, not only in relation to AIDS but also hepatitis and other infections, that many safety hypodermic needles have been devised. So many have been devised that organizations of health-care professionals and hospitals have published guides and standards for their design and selection. These guides and standards tend to evidence that no single best or adequate design solution has been found. This invention applies the best of such known guides and standards and in addition utilizes special experience and insight in the problem.

Although numerous, none of the known safety hypodermic devices provide a progressive needle-shaft lock, a needle-end lock, a needle-end shield and a shield-actuation means that can all be attached to a base of a conventional hypodermic needle for convenient one-handed use in the manner taught by this invention. Most are too bulky, inconvenient and ineffective in various limiting

SUMMARY OF THE INVENTION

In accordance with the present invention, it is contemplated that in light of the problems that have existed and that continue to exist in this field, objectives of this invention are to provide a safety hypodermic needle and shielding device which:

Can be attached conveniently and easily to a coupling base of a conventional hypodermic needle as part of a production or preparation process commercially prior to sale or use;

Can be attached conveniently and easily to a coupling base of a conventional hypodermic needle prior to use by a health-care worker or other user;

Is small and light in order to prevent obstruction or inconvenience of use;

Has a small perimeter that allows low-angle positioning of a syringe with a needle shank near parallel to a body of an individual on which it is used;

Is short to allow use of hypodermic needles without significant additional length;

Allows one-handed use of the syringe and actuation of the shielding device easily and conveniently;

Provides shaft-lock positioning of the shielding device along a needle shaft after release;

Provides end-lock positioning of the shielding device on a point end of hypodermic needles in a manner that prevents contact with the point end and prevents reuse of the hypodermic needles; and Is low in cost and convenient to store for later use.

This invention accomplishes the above and other objectives with a safety hypodermic needle and shielding device having a spring-loaded safety shield with a one-way locking means which prevents return of the safety shield from travel along a syringe-needle shaft and frown a point end of a syringe-needle shaft. One preferred one-way locking means is a pivot plate positioned in the shielding device with the syringe-needle shaft extended through a locking orifice in the pivot plate. A preferred spring for spring-loading the shielding device is at least one leaf spring expandable in a plane parallel to the syringe-needle shaft. A needle conduit in the shielding device is closed with a spring-actuated obstruction that prevents protrusion of the point end of the syringe needle after its use when it has been covered by the shielding device.

Other objects, advantages and capabilities of the invention will become apparent from the following description taken in conjunction with the accompanying drawings showing preferred embodiments of the invention.

BRIEF DESCRIPTION OF THE DRAWINGS

FIG. 6 is a top view of the FIG. 2 illustration;

FIG. 7 is a partial cutaway side view of a safety shield with a pivot plate;

FIG. 8 is a partial cutaway side view of a safety shield with a cover-spring lock;

FIG. 9 is an end view of a straight-walled leaf spring used for actuating the safety shield;

FIG. 10 is an end view of an arcuate-walled leaf spring used for actuating the safety shield;

FIG. 11 is a partial cutaway side view of a rotational-latch embodiment with the safety shield in cocked position and with the needle cannula attached;

FIG. 12 is a top view of the FIG. 11 illustration;

FIG. 13 is a partial cutaway side view of the rotational-latch embodiment with a safety shield having a cover-spring lock;

FIG. 22 is a partial top view of another embodiment of the invention showing a modified latch mechanism and a modified spring, showing the needle in a cocked ready-to-use position;

FIG. 23 is a partial vertical cutaway elevation view of the needle and safety shield of FIG. 22;

FIG. 24 is an elevation view of the needle of FIG. 22 shown in a released safety condition; and FIG. 25 is a vertical section view, showing sections partially broken away, of the needle cannula and leaf spring taken along lines a—a of FIG. 24.

DESCRIPTION OF THE PREFERRED EMBODIMENTS

Figure 1:
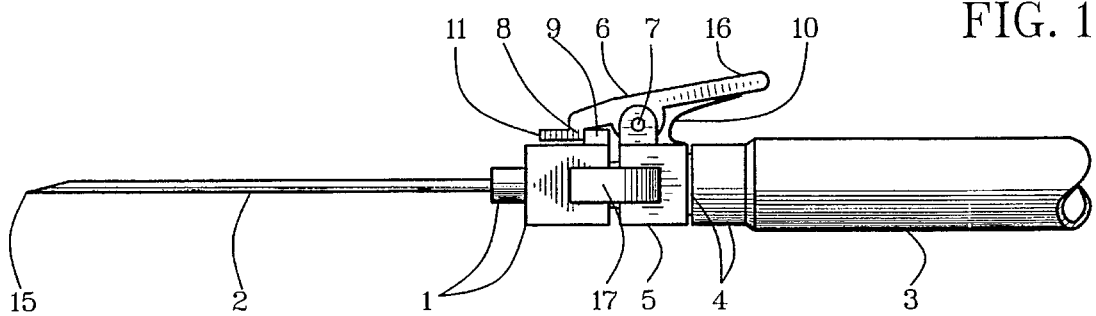
FIG. 1 is a side elevation view of a press-latch embodiment of this invention attached to a needle end of a syringe cylinder.

Referring to the drawings wherein like reference numerals designate corresponding parts throughout the several figures, reference is made first to FIGS. 1–6. A safety shield 1 has a needle conduit that is sized and shaped internally to encompass a select portion of a cannula shaft 2 that is attached to a syringe 3 with a conventional luer connector 4. A shield base 5 is attachable to the luer connector 4 intermediate the needle cannula shaft 2 and a needle portion of the luer connector 4 that is exposed beyond a syringe portion of the luer connector 4. The safety shield 1 and the shield base 5 are held together by a press latch 6 in the form of a lever pivotally attached to a latch fulcrum 7 and having a press-latch hook 8 that hooks onto a latch boss 9 where it is held by a latch spring 10.

The latch boss 9 provides a latch-related function of items that are referred to variously in the lock trade as a striker or a catch. It can have a variety of forms to provide this function in relation to this invention. Another form of this boss 9, employing a catch pin or striker pin is described later in relation to FIGS. 14–21.

The press latch 6 is safety-locked with a press-latch lock extension 11 that fits under a lock cover 12 in a raised portion of a cannula skirt 13 of a cannula sheath 14 that is positioned on the cannula shaft 2 prior to use. With the cannula sheath 14 attached as shown in FIGS. 3 and 4, the cannula shaft 2 is covered and the safety shield 1 cannot be released prior to use.

Figure 2:
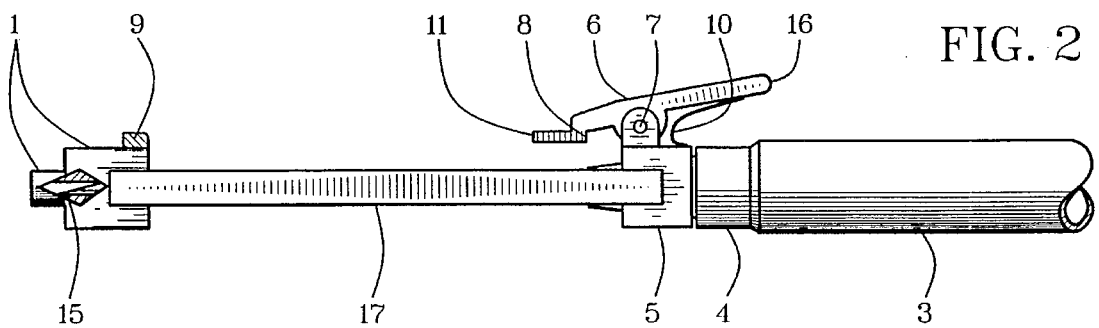
FIG. 2 is a side elevation view of the FIG. 1 illustration with a safety shield in a released condition and shown partly cutaway on an end of a hypodermic needle.
Figure 3:
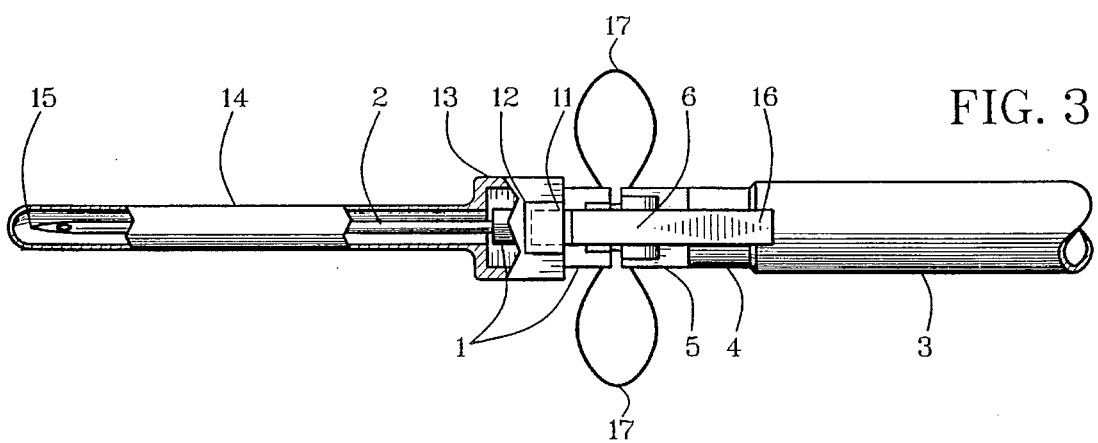
FIG. 3 is a top view of the FIG. 1 illustration with a partial cutaway view of a needle cannula added.
Figure 4:
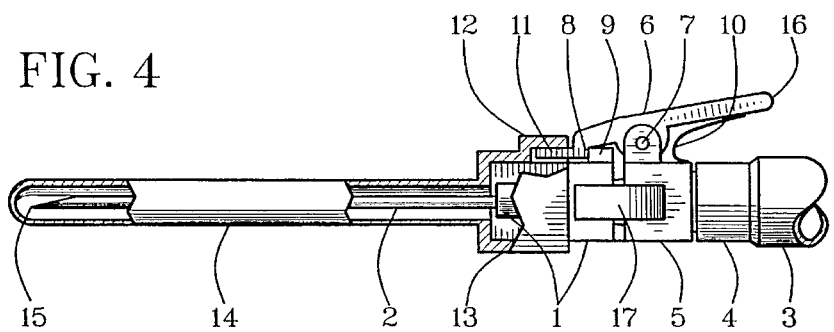
FIG. 4 is a side elevation view with a partial cutaway view of the FIG. 3 illustration showing a partial cutaway side view of a needle cannula on a cocked safety shield.
Figure 5:
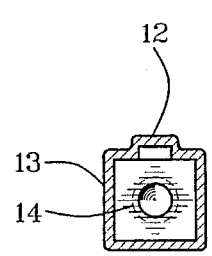
FIG. 5 is an end view of the needle cannula from a sheath-skirt end.

The safety shield 1 travels from a cocked position shown in FIGS. 1 and 3–4 to a shield position enclosing a needle point 15 as shown in FIGS. 2 and 6 when a handle 16 of the press latch 6 is pressed in opposition to the latch spring 10. Travel of the safety shield 1 is actuated by at least one leaf spring 17 as a shield spring that is biased in a looped condition as shown in FIGS. 1 and 3–4 until the handle 16 is pressed to remove the press-latch hook 8 from a latched relationship to the latch boss 9. Then the leaf spring 17 straightens out to a straight condition as shown in FIGS. 2 and 6. The safety shield 1 has a base end positioned in a direction of the shield base and a point end positioned in a direction of the needle point 15. While the leaf spring 17 is shown in FIGS. 1 and 12 as a double spring, the invention will work equally well if only one leaf spring is used.

The cannula skirt 13 can be variously attached to the safety shield 1 to prevent the skirt of the cannula sheath 1,t from coming off too easily and yet be removed conveniently. Conventional dimples matched to extrusions in matching surfaces is one recommended means for attachment.

Referring to FIGS. 7 and 11, return travel of the safety shield 1 can be prevented by a pivot plate 18 that can pivot between perpendicular and slanted positions relative to the cannula shaft 2 in a portion of the needle conduit that is sized and shaped as a pivot-plate cavity 19 inside of the safety shield 1. Perpendicular position is shown in solid lines and slanted position in dashed lines. An edge of a lock orifice 20 in the pivot plate 18 engages the cannula shaft 2 (as seen in FIG. 11) when the pivot plate 18 is in a slanted condition and prevents return travel in a direction towards the luer connector 4 from either the point 15 or from any position along the cannula shaft 2. The pivot plate 18 is a form of one-way shaft lock positioned in the needle conduit of the safety shield 1.

Reference is made here to FIGS. 8 and 13. Alternatively, return travel of the safety shield 1 can be prevented by a cover spring 21 attached to a wall of a cover-spring cavity 22 in the safety shield 1. The cover spring 21 can be a leaf spring with cover plate 23 extended about perpendicularly to a body of the cover spring 21 that is attached to the wall of the cover-spring cavity 22. With the cover plate 23 biased against the cannula shaft 2, the cover spring 21 will position the cover plate 23 over a needle point 15 and prevent return travel of the safety shield 1 or exposure of the needle point 15 after the safety shield 1 has been actuated by the leaf spring 17. Covering conditions of the cover spring 21 and the cover plate 23 in relation to a needle point 15 are shown in dashed lines.

The leaf spring 17 can have either a straight cross section from side-to-side as shown in FIG. 9 or an arcuate cross section laterally from side-to-side as shown in FIG. 10. Although both shapes of leaf springs 17 can be designed for appropriate spring tension, the arcuate leaf spring 17 shown in FIG. 10 has a higher capacity per spring strength to maintain straightness linearly from-end-to-end and, therefore, provides greater protection against reuse of the cannula shaft 2 by circumventing the lock means described in relation to FIGS. 7–8.

In the description of the springs 17 and 21, and of the pivot plate 18, the preferred material from which these items are made is a steel based metal. It has been found that if critical parts such as these are made from a thermoplastic material, the parts will not exhibit the required performance since thermoplastic materials are quite temperature sensitive.

Referring to FIGS. 11–13, a rotational latch 24 can be employed as an alternative to the press latch 6 described in relation to FIGS. 1–4 and 6. Either the press latch 6 or the rotational latch 24 can be used interchangeably with a safety shield 1 having either a pivot plate 18 or a cover spring 21. Also, the same cannula sheath 14 with the same lock cover 12 can be employed with either press latch 6 or rotational latch 24. All parts are interchangeable for use with either the press latch 6 or the rotational latch 24.

The rotational latch 24 is rotatable on a latch axle 25 extended from the shield base 5. A rotational-latch hook 26 can be positioned against the latch boss 9 and then rotated either direction to a side of the latch boss 9 in order to release the safety shield 1. With the lock cover 12 of the cannula skirt 13 positioned on a rotational-lock latch 27 extended from the rotational-latch hook 26, however, the rotational latch 24 can not be rotated to release the safety shield 1. It is safety-locked with the same means as for safety-locking the press latch 6.

Referring to FIGS. 14–21, a single-spring embodiment has a single leaf spring 17 with a distal end anchored to a catch pin 28 on a catch-pin boss 20 that is extended from a top surface of a safety shield 1. The catch pin 28 is elevated sufficiently to provide space between the top surface of the safety shield 1 and the catch pin 28 for juxtaposed insertion of both a spring-release latch 30 and a lock insert 31. The spring-release latch 30 is attached pivotally to a single-spring mount 32 on the shield base 5. A proximal end of the single leaf spring 17 can be attached to a spring-mount pin 33 on the single-spring mount 32. A latch handle 34 is extended upward from a latch pin 35 with which the spring-release latch 30 is attached pivotally at a position intermediate the catch pin 28 and the spring-mount pin 33.

A safety shield 1 having a pivot plate 18 and a safety shield 1 having a cover spring 21 are operated the same way and have the same cannula skirt 13 and cannula sheath 14. With the latch handle 34 in an upward or substantially vertical attitude, the lock insert 31 on a cannula skirt 13 is positioned under the spring-release latch 30 to provide needle coverage and to prevent unintended release of the spring-release latch 30 prior to use of the cannula shaft 2. Then when use of the cannula shaft 2 is intended, the cannula sheath 14 with the cannula skirt 13 and the lock insert 31 extended from it is removed linearly. After use of the cannula shaft 2 for health-care purposes, the single leaf spring 17 is pushed slightly forward in a direction towards the cannula shaft 2. This forward pushing of the single leaf spring 17 causes contact of the single leaf spring 17 with the latch handle 34 in a rotational travel that releases the spring-release latch 30 from latching relationship with the catch pin 28. This allows the single leaf spring 17 to push the safety shield 1 to a point end of the cannula shaft 2 with straightening tension of the single leaf spring 17.

Figure 14:
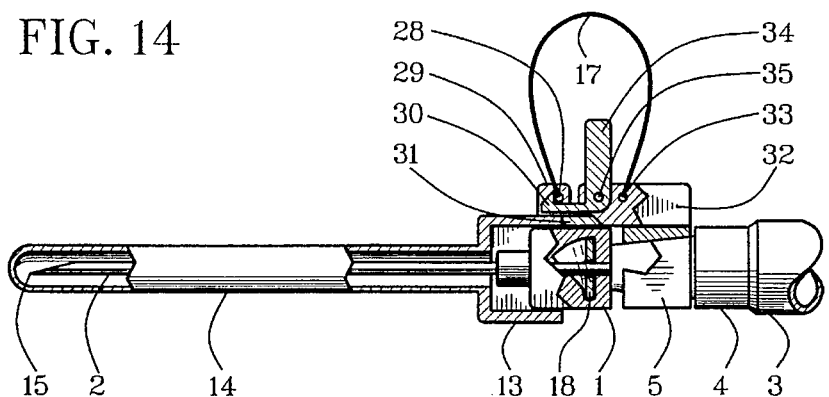
FIG. 14 is a partial cutaway side view of a single-spring embodiment with a pin boss, an insert locking means and a pivot-plate cover-locking means.
Figure 15:
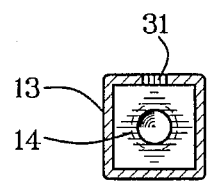
FIG. 15 is an end view of a cannula skirt for the single-spring embodiment.
Figure 16:
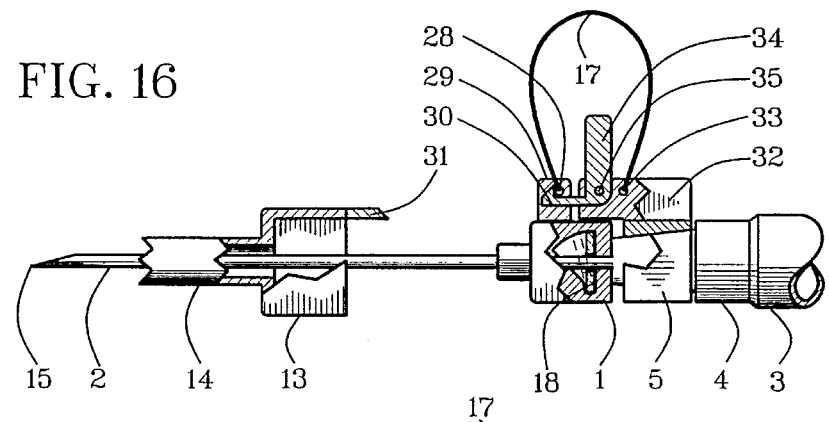
FIG. 16 is a partial cutaway side view of the FIG. 14 illustration with the cannula skirt in sliding relationship to the needle shaft.
Figure 17:
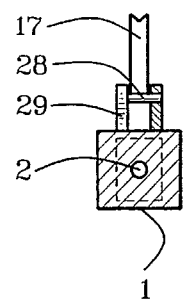
FIG. 17 is a luer-end view of a safety shield for a single-spring embodiment with a pin boss, an insert locking means and a pivot-plate cover-locking means.
Figure 18:
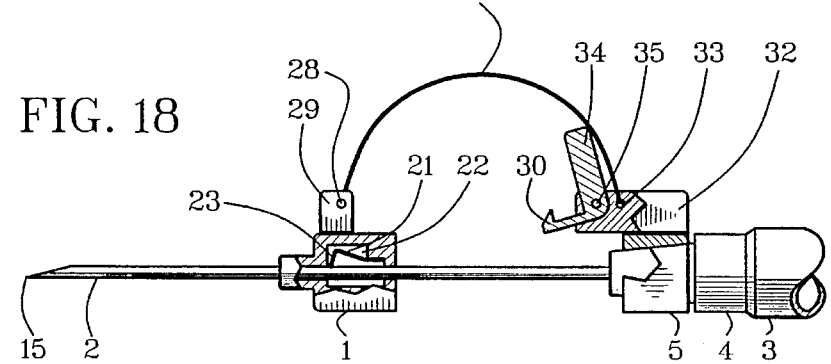
FIG. 18 is a partial cutaway side view of a single-spring embodiment with a pin boss, an insert locking means and having a safety shield with a cover-spring for a cover-locking means in sliding relationship to the needle shaft.
Figure 19:
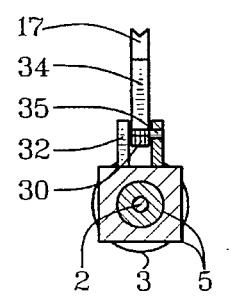
FIG. 19 is a needle-end view of a luer with a spring-release latch positioned upward for a locked mode.
Figure 20:
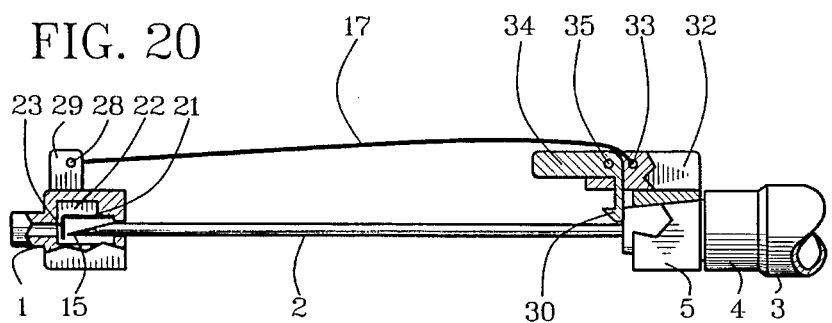
FIG. 20 is a partial cutaway side view of the FIG. 18 illustration in needle-point-covering mode.
Figure 21:
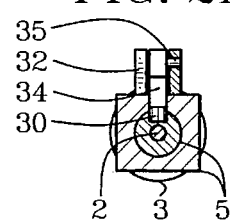
FIG. 21 is the FIG. 19 illustration with the spring-release latch positioned downward for disengagement in a needle-point-covering mode.

FIG. 14 shows a locked mode of the lock insert 31 in relationship to the spring-release latch 30. In FIG. 16, the lock insert 31 has been removed from its locking relationship and the cannula sheath 14 is being removed to render the cannula shaft 2 ready for use. In FIG. 18, the single leaf spring 17 has been pushed against the latch handle 34, causing the latch 30 to disengage from the catch pin 28 and the single leaf spring 17 has pushed the safety shield 1 towards the needle-point 15 end of the cannula shaft 2. In FIG. 20, single leaf spring 17 has straightened out and pushed the safety shield 1 to a covering position on the point end 15 of the cannula shaft 2. Return travel of the safety shield 1 is then prevented by either a cover plate 23 on a cover spring 21 as shown in FIGS. 8, 13, 18 and 20 or by binding action of a pivot plate 18 as shown in FIGS. 7, 11, 14 and 16 on the cannula shaft 2. Prevention of return travel prevents exposure of the cannula shaft 2 after it has been used.

Disengaging the pivot plate 18 or the cover spring 21 for cocking the safety shield 1 in production prior to use can be accomplished with a construction orifice that allows positioning of an instrument against either the pivot plate 18 or the cover spring 21. The construction orifice is then closed. It does not appear in these illustrations because it is not a functional part of an operative safety hypodermic needle and because the orifice can be positioned variously in the safety shield 1. Intentionally, the safety shield is constructed not to reveal positioning of the closed construction orifice to users or to would-be subsequent users.

Referring to FIGS. 22–25, a different release mechanism is shown along with a modified leaf spring actuating system, wherein the leaf spring 17a, similar to the spring 17 shown in FIG. 10, also acts as the biasing arm against the safety shield 36 to prevent the safety shield from being pushed back behind the needle point 15 once the safety shield has been released to thereby prevent the exposure of the needle point 15 after use of the hypodermic syringe.

It is important to note that certain patents of the prior art utilize spring biasing systems wherein the spring is shown biased against plastic parts of the hypodermic needles and such, should the needle be stored for considerable periods of time, could be detrimental to the safety of the needle. Maintaining biasing spring stress upon plastic parts will cause deformation over a period of time and could either destroy the effectiveness of the safety system, or could cause malfunctions. Therefore, there needs to be a very strong plastic material provided in this invention, which will resist deformation because of the stored biasing energy of the spring on the plastic parts, or it is contemplated that one should utilize metalized parts in certain aspects of the invention.

The embodiment of FIGS. 22–25 shows the syringe 3 and luer connector 4 to which the safety latch mechanism is attached. An integral part of the luer arc luer side plates 37 on either side of the luer 4, which project axially along the cannula shaft 2 to form the proximal end of the bifurcated latch system. Attached to a forward portion of the luer side plates 37, is a latch member 38 comprising a bifurcated member having a latch handle 39, a latch actuator surface 40, latching arms 41 and spring-release latch hooks 42. The latch member 38 is connected to the luer side plates by means of a latch fulcrum pin 43, which pin projects through mating holes on each of the luer side plates and projects through the rear most portions of the latching arms 41 to provide a pivoting arrangement for the latch member 38.

In the latched position shown in FIG. 23, the leaf spring 17a is folded so that the energy is stored therein and ready for use. The latch member 38 is cocked so that the spring-release latch hooks 42 wrap around catch pin 44, which pin projects through mating holes in the pair of shield side plates 45, which are connected to either side of the safety shield 36 much in the manner the luer side plates 37 are connected to the luer 4. The shield side plates 45 will preferably have a shape which is similar to the luer side plates 37 in order to make the syringe aesthetically pleasing and to balance the operation thereof. When the latch hooks 42 are positioned about catch pin 44, the syringe is in the ready-to-use position and, after use thereof, the operator will effect the safety function by pressing a thumb or other finger of the hand holding the syringe against the latch actuator surface 40 of the latch handle 39 so that the pressure thereon is essentially parallel to the direction of cannula shaft 2, thereby rotating the latching arms 41 about latch fulcrum pin 43 to thereby rotate the spring-release latch hooks 42 frown catch pin 44.

Once the latch hooks 42 are completely clear of catch pin 44, the stored energy of leaf spring 17a will act against the free safety shield 36 and move it along cannula shaft 2 to a point where the safety shield fully covers needle point 15 as shown in FIG. 24. At this point, the needle is in a safe condition and is not readily reusable, and the needle point 15 is in no position to accidentally prick a user.

An important feature of this embodiment is that the spring 17a may be attached to latch fulcrum pin 43 and the catch pin 44 in one of two ways. Both manner of attaching the spring will be fully described at this point. In FIG. 24, in the first version of the spring attachment, it is seen that spring 17a is attached between latch fulcrum pin 43 and catch pin 44 wherein the longitudinal centerline of the spring lies below the axis of pins 43 and 44. As shown, the spring curves upwardly around the pins by pin engaging ends 46. In this manner of attachment, it is easy to see that the longitudinal centerline of the spring lies below a line connecting the center point axis of each pin. When spring 17a is in the released safety position, as shown in FIG. 24, any backward pressure against safety shield 36 will be transmitted to spring 17a which will resist any movement of the safety shield 36, and spring 17a acts as a column and will resist deformation because of the concave shape thereof. In the version of the spring shown in FIG. 24, wherein the longitudinal centerline of the spring 17a lies below the axis of pins 43 and 44, should overpressure be applied to safety shield 36, the spring would only tend to deform downwardly in a direction toward cannula shaft 2. Because of the proximity of spring 17a to cannula shaft 2, very little deformation of the spring will take place, because the spring will impact the needle and will thereby prevent any further deformation of the spring and will likewise prevent further rearward movement of the safety shield 36.

In a second version of the attachment of spring 17a to pins 43 and 44, it is anticipated that the longitudinal centerline axis of the spring can be configured so that the centerline lies on a line which connects the centerline axis of pins 43 and 44. In this configuration, the pin engaging ends 46 would be configured so that the spring, once attached, would be raised to an imaginary line connecting the centerline axis of pins 43 and 44. In this version, any rearward pressure on safety shield 36 would impact spring 17a and spring 17a would act as a pure column to thereby resist, even more rigidly, any deformation of the spring either upwardly away from the needle or downwardly toward the needle. Such a system would thusly provide a fail safe safety needle in which the safety shield 36 cannot be inadvertently moved away from the needle point 15 once the shield has been released from the cocked position. In addition, the locking mechanism in the safety position is exceedingly simple and reduces the number of parts of the needle considerably. It will also be appreciated that the cannula sheath 14, shown in other figures herein, may well be modified only slightly to fit the syringe shown in FIGS. 22–24. It should also be noted that the length of the springs 17 and 17a will limit the overall travel of safety shields 1 and 36, and such travel limitations will provide for a shielded tip of enhanced safety.

A variety of known materials and combinations of materials can be employed for production and use of this invention. Additional materials being developed are foreseeable also. While various materials could be recommended, it is believed that those skilled in the art can make a design choice of materials for their particular objectives.

Various modifications may be made of the invention without departing from the scope thereof and it is desired, therefore, that only such limitations shall be placed thereon as are imposed by the prior art and which are set forth in the appended claims.

What is claimed is:

1. A safety hypodermic needle comprising:

a needle cannula shaft having a proximal end and a distal tip, a latch member assembly juxtaposed to the proximal end of the needle cannula shaft, a safety shield having a proximal end and distal end, a through aperture connecting the proximal end and the distal end, the safety shield being slidably moveable along the needle cannula shaft from a first position juxtaposed to the proximal end of the needle cannula shaft, to a second position where the distal tip of the needle cannula shaft is positioned intermediate the proximal end and the distal end of the safety shield, a connecting member attached to the proximal end of the needle cannula shaft, a pair of side plates flanking the connecting member to define a space between the side plates, the side plates having a supporting portion therein, the supporting portion of each side plate having a through aperture, each aperture being in axial alignment with one another, a single latch fulcrum pin being placed in each aperture and spanning the space between the side plates to interconnect the pair of side plates, the latch fulcrum pin having a longitudinal centerline defining the axis thereof, the proximal end of the safety shield having a pair of side plates flanking the safety shield and attached thereto to define a space between the side plates, the safety shield side plates having a supporting portion therein, the supporting portion of each safety shield side plate having a through aperture, each aperture being in axial alignment with one another, a single catch pin being placed in each aperture and spanning the space between the safety shield side plates to interconnect the pair of side plates, the catch pin having a longitudinal centerline defining the axis thereof, the lateral member assembly comprising a bifurcated latch member having spaced apart latching arms, the latching arms having a proximal end comprising a latch handle with a latch actuator surface bridging together the spaced apart latching arms and further having an aperture in the proximal end of each latching arm wherein the apertures are in axial alignment and are in rotational engagement with the latch fulcrum pin, the latching arms further having a distal end comprising spring-release latch hooks, the latch hooks having a surface for releasably engaging the catch pin of the shield side plates, and spring means connected between the latch fulcrum pin and the shield side plate catch pin for urging the safety shield along the needle cannula shaft toward the second position.

2. The safety hypodermic needle as claimed in claim 1, the spring means comprising an elongated, concave cross-sectioned spring.

3. The safety hypodermic needle as claimed in claim 2, the spring having a longitudinal centerline defining the center of the spring, the spring being connected to the latch fulcrum pin and the shield side plate catch pin so that the longitudinal centerline of the spring intersects the longitudinal centerline axis of both the latch fulcrum pin and the side shield plate catch pin.

4. The safety hypodermic needle as claimed in claim 3, the spring having a longitudinal centerline defining the center of the spring, the spring being connected to the latch fulcrum pin and the shield side plate catch pin so that the longitudinal centerline of the spring is displaced in a direction toward the needle cannula shaft from the longitudinal centerline axis of both the latch fulcrum pin and the shield side plate catch pin.

* * * * *